(12) United States Patent
Frayne

(10) Patent No.: US 11,254,958 B1
(45) Date of Patent: Feb. 22, 2022

(54) **METABOLIC ENGINEERING OF *E COLI* WITH THIO-PHOSPHATE**

(71) Applicant: Elizabeth Gay Frayne, La Mirada, CA (US)

(72) Inventor: Elizabeth Gay Frayne, La Mirada, CA (US)

(73) Assignee: Elizabeth Gay Frayne, La Mirada, CA (US)

( * ) Notice: Subject to any disclaimer, the term of this patent is extended or adjusted under 35 U.S.C. 154(b) by 298 days.

(21) Appl. No.: 16/409,528

(22) Filed: May 10, 2019

Related U.S. Application Data

(60) Provisional application No. 62/687,664, filed on Jun. 20, 2018.

(51) Int. Cl.
| | |
|---|---|
| *C12P 13/24* | (2006.01) |
| *C12P 13/22* | (2006.01) |
| *C12P 5/00* | (2006.01) |
| *C12P 7/64* | (2006.01) |
| *C12P 19/28* | (2006.01) |
| *C12P 7/6409* | (2022.01) |

(52) U.S. Cl.
CPC ............... *C12P 13/24* (2013.01); *C12P 5/007* (2013.01); *C12P 7/6409* (2013.01); *C12P 13/227* (2013.01); *C12P 19/28* (2013.01)

(58) Field of Classification Search
CPC ......... C12P 13/24; C12P 5/007; C12P 7/6409; C12P 13/227; C12P 19/28
See application file for complete search history.

(56) References Cited

U.S. PATENT DOCUMENTS

| | | |
|---|---|---|
| 7,125,982 B1 | 10/2006 | Frayne |
| 7,691,631 B2 | 4/2010 | Frayne |
| 8,088,602 B1 | 1/2012 | Frayne |

*Primary Examiner* — Ganapathirama Raghu

(57) ABSTRACT

The present invention describes the use of thio-phosphate in the metabolic engineering of *E. coli*. Thio-phosphate can be used to increase the metabolic flux in important synthetic pathways to enhance the production of bioproducts. The pathways impacted include the following: fatty acid synthesis, isoprenoid syntheses, Vit K2 synthesis, ribonucleotide synthesis, and the synthesis of phosphoribosyl pyrophosphate (PRPP) derivatives like 5-aminoimidazole-4-carboxamide (AICA riboside), histidine, and tryptophan. Thus, thio-phosphate can be used to assist in the production of these molecules and/or their derivatives. Enhanced production of AICA in *Bacillus megaterium* is also demonstrated.

5 Claims, 3 Drawing Sheets

FIGURE 2

| Fold Changes in Specific Gene Transcripts in TP versus Control Cells ||||||
| Category | RNA Seq | Microarray | Category | RNA Seq | Microarray |
| RNA Metabolism ||| RNases |||
| udp - degrades urd | | -3.2X | rnb | | 1.4X |
| upp | | 2.0X | rnr | 1.36X | 2.5X |
| pyrF | | 3.7X | pnp | 3.8X | 1.8X |
| pyrH | 3.5X | 1.2X | rhlb | | -1.1X |
| pyrG | 2.1X | 1.6X | rne | 26X | 2.6X |
| adk | 3.4X | 1.5X | | | |
| purB | 35X | 1.5X | | | |
| RNA Processing & Modification Enzymes ||||||
| dusB | 1.8X | 4.2X | | | |
| tadA | | 3.1X | | | |
| trmA | | 2.8X | | | |
| rlmH | | 3.4X | | | |
| yqgf | 4.6X | 3.4X | | | |
| cspA | 1.6X | 3.1X | | | |
| Protein Synthesis Initiation Factors ||||||
| infB | 3.1X | 3.1X | | | |
| ycih | 3.3X | 8.0X | | | |
| PRPP Derivatives ||||||
| trpA | 1049X | -2.1X | | | |
| trpB | 1955X | -1.5X | | | |
| trpC | 606X | -2.4X | | | |
| trpD | 443X | -1.3X | | | |
| trpE | 541X | -1.3X | | | |
| hisA | 6.2X | 1.1X | | | |
| hisB | 162X | 1.1X | | | |
| hisC | 117X | 1.0X | | | |
| hisD | 10.9X | 1.1X | | | |
| hisH | 28X | 1.4X | | | |
| hisI | 5X | -1.0X | | | |
| hisG | 4.6X | 1.4X | | | |
| purK | 17X | 1.1X | | | |
| purE | 47X | 1.1X | | | |
| purB | 35X | 1.5X | | | |

FIGURE 3
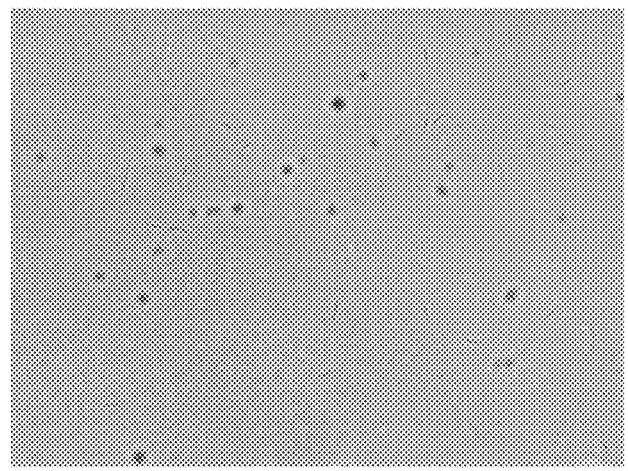
Fig. 3A
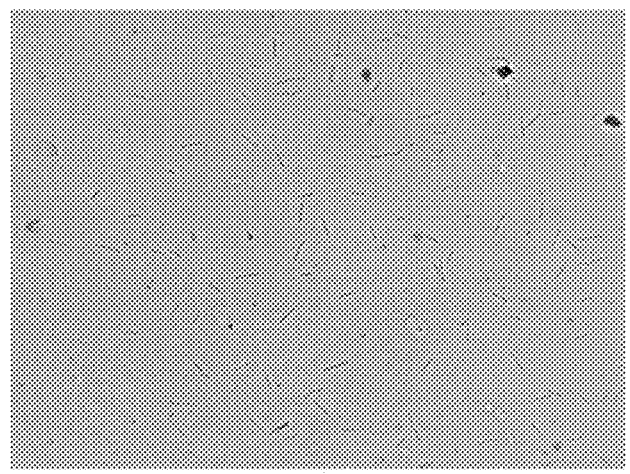
Fig. 3B
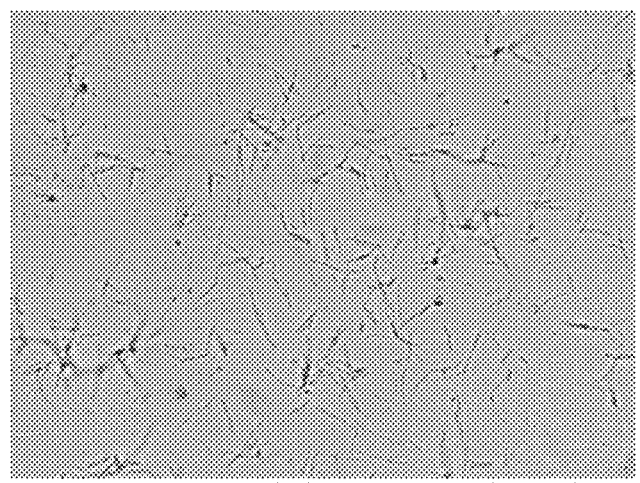
Fig. 3C

METABOLIC ENGINEERING OF *E COLI* WITH THIO-PHOSPHATE

The present invention claims the benefit of the provisional application 62/687,664 filed Jun. 20, 2018. The present invention relates to the use of microbes to produce organic compounds via metabolic engineering. Microbes can be manipulated to produce chemicals, including novel chemicals, via creating or mutating genetic pathways and their regulatory components. Synthetic biology is a branch of metabolic engineering that introduces entire pathways or parts thereof from other organisms into host organisms of choice. The pathway genes of interest may also be artificially created in vitro and manipulated for optimum output at the RNA or protein level prior to their reintroduction in vivo. Optimizing output often involves redirecting the metabolite flux from one pathway into another.

BACKGROUND OF THE INVENTION

Thio-phosphate is readily taken up by a variety of organisms resulting in the in vivo synthesis of nuclease resistant nucleic acids (Frayne, 2016, *Mol. & Cell. Biochemistry*. 415, 111-117). This raises the possibility that reduced turnover of RNA may impact interconnected pathways. For example, phosphoribosyl pyrophosphate (PRPP), an important intermediate in nucleic acid synthesis, may accumulate due to less turnover of RNA in the cell. This could then lead to increased levels of histidine and tryptophan which use PRPP as a precursor, because less PRPP being siphoned off to make nucleic acids (Frayne, 2016, Res. & Reviews: Res. J. Bio.). Similarly, increased levels of GTP as the result of less turnover of RNA in the cell may lead to enhanced riboflavin synthesis.

This relatively simple approach relies on using thio-phosphate as a replacement for phosphate in feed sources (Frayne, U.S. Pat. Nos. 7,125,982; 7,691,631; 8,088,602). Thio-phosphate is then incorporated into nucleic acids creating phosphorothioate linkages that are nuclease resistant. Thio-phosphate appears to be universally accepted as a phosphate source. It also results in a global shift in the distribution of proteins with less abundant proteins being favored over more abundant proteins.

However, these changes appear to be largely the result of transcriptional regulatory changes incurred via thio-phosphate rather than to differential mRNA stabilization (see below).

The use of thio-phosphate results in profound transcriptional changes in *E coli* that ultimately redirect more metabolites towards the synthesis of fatty acids, isoprenolds, PRPP and its derivatives, and vit K2 (Frayne, 2018 AIChe SEED conference, Scottsdale, Ariz.). The isoprenoids are used to make more undecaprenyl phosphate, a lipid carrier molecule transporting hydrophilic peptidoglycan precursor molecules. The type II secretion pathway normally not active in K12 strains of *E coli* is also induced. Increased fatty acid synthesis may lead to increased lipoproteins on the surface and/or phospholipids.

SUMMARY

The present invention enables the redirection of metabolites towards specific pathways via the use of thio-phosphate. In *E. coli*, the targeted pathways are those that use PRPP as a primary intermediate such as the amino acids histidine and tryptophan, as well as the ribonucleotide AICAR. Also included are increases in the transcripts for genes involved in the pathways for fatty acid synthesis and isoprenoids.

BRIEF DESCRIPTION OF THE DRAWINGS

FIG. 2. Shows a summary of the RNA seq and microarray results for genes involved in RNA metabolism and PRPP derivatives.

FIG. 3. FIG. 3A depicts control bacteria at 2 hrs. FIG. 3B depicts the paired phenotype seen in bacteria grown in LB with TP at 12 hrs. FIG. 3C depicts the filamentous phenotype seen at 12 hr in minimal media with TP (see methods).

DESCRIPTION OF PREFERRED EMBODIMENTS

Figure 1:
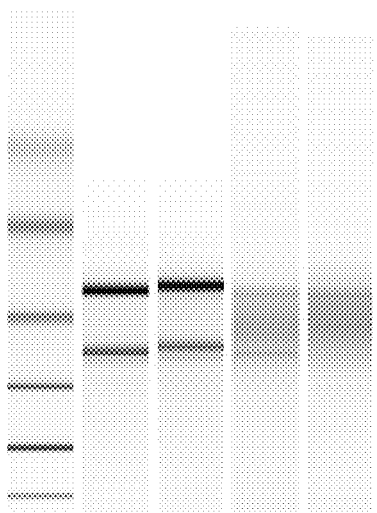
FIG. 1. Lane M shows markers ranging from 200 to 4000 bp. Lane C shows control RNA at 6.2 ng/ul and lane T shows 5.4 ng/ul of TP treated RNA. Lanes CX and TX show samples in which much of the ribosomal RNA was depleted. CX is control RNA at 0.81 ng/ul and TX is TP treated RNA at 0.49 ng/ul.

Thio-phosphate is envisioned to enhance the metabolic flux of metabolites in designated pathways of *E. coli*. These pathways include those used to produce natural products or synthetic products depending on how the host organism is modified (Leproust, E. 2016, CEP, 112:30-35). This bacterium is easily manipulated and serves as a chassis for synthetic biology projects used in the production of various organic compounds. Special interest revolves around those compounds that replace petroleum derived products and thus are more sustainable for the environment.

PRPP is a critical biochemical intermediate in several reactions (Hove-Jensen, et al. 2017, MMBR, 81: 1-82). It typically serves as a donor of N glycosidic bonds. It is used in the synthesis of his, trp, NAD, tetrahydromethanopterin, arabinosyl monophosphodecaprenol, and certain aminoglycoside antibiotics. Thio-phosphate presumably leads to an increase in PRPP levels via reduced turnover of RNA. In *E coli*, use of thio-phosphate enhances the production of histidine and tryptophan as evidenced by increases in the transcript levels of genes required for the synthesis of these products. Flux in through either of these pathways can be preferentially enhanced by mutation of the appropriate genes. For instance, enhanced flux towards histidine could be achieved by using a mutation in trypD which consumes PRPP need for the synthesis of tryptophan. Note AICAR might negatively regulate hisG as well (Malykhet al (2018) Microbial Cell Factories, 17(1):42). Conversely, enhanced flux towards tryptophan could be achieved via mutations in hisG. This method may be particularly useful for tryptophan production in general, as regulation of this operon is variable in different species.

PRPP is also used in the synthesis of AICAR. Increased levels of PRPP could also lead to enhanced production of AICR and AICA in de-regulated mutants designed to secrete AICA the unphosphorylated version of this compound. This idea was tested using a strain of *Bacillus megaterium* (ATCC 15117; U.S. Pat. No. 3,238,110) that secretes AICA into the media. With thio-phosphate the levels were increased 2× on a per cell mass basis compared to normal phosphate containing culture media. Further increases may be obtained using mutants that reduce the flow towards histidine and tryptophan such as mutants equivalent to hisB in *E coli*, which still allows for AICAR production by hisH and hisF genes. Also, mutations in the tryptophan pathway could also increase the flux towards AICA. Alternatively, enhanced production of AICAR may be obtained by adding histidine or tryptophan to the culture media (Gotts & Love (1954) Journal of Biological Chemistry 210:395-405). Furthermore, these pathways could also be manipulated via genetic engineering methods which allow the introduction of modified genes and pathways with enhanced and/or novel capabilities (Szymanski (2018), Life Sciences, Society and Policy 14:15; Pedrolli, Danielle B, Ribeiro, Nathan V, Squizato, Patrick N, de Jesus, Victor N, Cozetto, Daniel A. (2019) Trends in Biotechnology, Oxford Vol. 37, Iss. 1; de Lorenzo, Victor (2018). Life Sciences, Society, and Policy; Heidelberg Vol. 14, Iss. 1: 1-16.

Other strains have been identified as AICA producing such as *Bacillus subtilis* (ATCC 15116, ATCC 15115; Sheremet et al (2011) J Ind Microbiol Biotechnol 38: 65). *Brevibacterium ammoniagenes* (ATCC 6871, ATCC 21106, ATCC 21105, U.S. Pat. No. 3,748,232). Also strains of *E coli* have been found which secrete this compound (Slotnic & Sevag, (1955) Archives of Biochem & Biophys 57:491-495). B-96 or ATCC 13863 is a particulary good candidate as it requires both tryptophan and a purine for growth (Gots & Love (1954), J. Biol. Chem. 210: 395-404. Any of these may be useful in the production of AICA using thio-phosphate.

Furthermore, the use of thio-phosphate results in increased concentrations of ribonucleosides and ribonucleotides as increased levels of transcripts for genes involved in their synthesis are seen in thio-phosphate treated cells. Synthesis of UTP, CTP, and ATP were enhanced the most. GTP did not appear to be significantly elevated as several genes involved in the synthesis of riboflavin, which requires GTP, did not appear to be significantly elevated, namely, ribD, ribB, and ribE as well as ribF used to form FAD. Nevertheless, this approach may be useful to enhance the production of ribonucleotides via the induction of their secretion in *E coli* with various agents such as streptomycin and 6-azauracil (Ogata et al, 1962, Agr. Biol. Chem. Vol 26: 586-595).

The use of thio-phosphate also increases the expression of *E. coli* genes involved in fatty acid synthesis. This could be used to increase fat or TAG production, particularly in a Tes mutant. This is because Tes Is also elevated and results in an increase in free fatty acids. Increased production of fatty acids has various applications, such as enhanced production of fat derived biofuels such as fatty alcohols, waxes, alka(e)nes and biodiesel (Jansen and Steinbuchel, 2014, Biotechnology for Biofuels, 7:7; Kalscheuer, 2006, Appl. Environ. Microbiol., 72(2): 1373-1379; Janβen, & Steinbüchel, Appl Microbiol Biotechnol (2014) 98: 1913. https://doi.org/10.1007/s00253-013-5460-2). It is possibility that the energy savings with reduced RNA turnover, could lead to an increased energy charge in the cell that enables more lipid synthesis in the cell.

Another pathway enhanced in thio-phosphate treated *E coli* is the production of isoprenoids. In *E. coli* this is via the non-mevalonate pathway. Isoprenoids are used in the synthesis of many compounds such as vitamin K, steroids, coenzyme Q10, vit A, carotenoids, quinones, lanosterol derivatives, terpenoids, polyisoprenes, squalene, non-natural isoprenes, etc. These can lead to pharmaceutical, nutraceuticals, and fragrances (Wong, et al. 2017, doi: 10.1007/978-3-319-31421-1_219-2). Thus, any pathway utilizing isopentenyldiphosphate (IPP) and dimethyallyl diphosphate (DMAPP) may benefit from an increase in these intermediates (Martin, et al., 2003, Nat. Biotech, 21:796-802; Kirby and Keasling, 2009, Ann. Rev. of Plant Bio., 60:335-355, Lund et al 2019, ACS Synthetic Biology, DOI: 10.1021/acssynbio.8b00383). The mevalonate pathway has also been introduced into *E. coli* and used to make isoprene, amorpha-4,11-diene, taxadiene, limonene, carotenoids, and long-chain isoprenoid pyrophosphates (Korman et al, 2014, Protein Science 2: 576-585). Antisense RNA has also been used to manipulate the production of isoprene in *E coli*. (Liu, 2015, RSC Adv. 5: 74892-74898).

EXPERIMENTAL

Methods

Growth Conditions

*E coli* K12 bacteria were grown in high citrate minimal media with 5.4 g/L of thiophosphate or 2.4 g/L of Na2HPO4 for up to 12 hrs. The use of high citrate media was chosen to help lower the total amount of thiophosphate needed for growth when compared to regular M9 media (1). The media is prepared as follows: thiophosphate, 5.4 g/L; KCL 1.5 g/L; $(NH_4)_2SO_4$, 2 g/L; sodium citrate $2H_2O$, 10 g/L. Adjust the pH to 7.5 and sterile filter the solution. Then add the following: $MgSO_4$-$7H_2O$, 0.2 g/L (sterilized separately as a conc. solution); glucose, 2 g/L sterilized separately by filtration). Glucose can also be sterilized by autoclaving separately. $CaCl_2$ (11 mg/L) is also be added as needed.

*Bacillus megaterium* was grown using a modified minimal media. In particular, the media contained: glucose, 60 g/L; KCL 1 g/L; MgSO4 0.4 g/L; peptone, 2 g/L; adenine, 0.25 g/L; NH4CI 8 g/L, urea, 3 g/L, calcium chloride, 0.5 g/L; as well as ferrous sulfate and manganese sulfate at 0.005 g/L. Thio-phosphate was added at levels between 2-6 g/L. For controls NaH2PO4 was add at 1 g/L.

rRNA Depletion

Total RNA was isolated using Bioline's ISOLATE II RNA mini kit. The quality of the RNA used had a RIN of at least 7 via the Agilent analyzer. The rRNA ratio (23s/16s) was at least 1.6. Note small RNAs like SS RNA were not retained under the conditions used. For rRNA depleted preparations, Ribominus (Invitrogen) was then used to deplete 23S and 16S rRNA. The ribosomal depleted RNA was then concentrated with the kit's concentration module prior to gel analysis.

Transcriptomic Methods

Both Microarray and RNA seq analysis was performed. Total RNA was used for both studies. For microarray studies, raw Affymetrix CEL files (*E. coli* Genome 2.0) were normalized to produce probeset-level expression values for all probesets with Expression Console (version 1.4.1.46), using the Robust Multiarray Average (RMA) and Detection Above BackGround (DABG) (Irizarry R. A et al. 2003, Biostatistics 4(2): 249-64. doi:10.1093/biostatistics/4.2.249). The analysis was limited to 10,112 *E. coli* probesets interrogated by the array. Fold changes were computed using the R environment for statistical computing (version 2.15.1) by Boston University Microarray and Sequencing (CTSA grant #1UL1TR001430).

For RNA seq analysis the RNA library was prepared using Illumina's TruSeq Stranded mRNA library prep (Illumina, 2010) without selection. The sequencing platform was HiSeq 2500 with a read format of PE 2×150. The coverage was at least 40 million per sample without rRNA depletion. A custom software build (Omegabioservice) of rRNA and tRNA sequences for reference mapping was used to more rapidly map rRNA sequences and avoid compression.

Results

Previous work suggested the presence of thiophosphate leads to higher levels of mRNA relative to ribosomal RNA in cells, due to the enhanced stability of mRNAs containing phosphorothioate nuclease resistant linkages. To further examine this idea, an Agilent analyzer was used to analyze the profiles of total RNA from control cultures and thiophosphate treated cultures (FIG. 1). It was evident that in *E. coli*, there was an increase in the non-ribosomal fraction, particularly between the 16S and 23S ribosomal RNAs, which was even more evident in ribosomal RNA depleted samples (FIG. 1). Quantitative analysis indicated the fraction of 16S and 23S rRNA in the profile of total RNA was depleted in TP cultures relative to controls. The average of two replicates indicated that these ribosomal RNAs represented 51.3% (49.4, 53.2) of the total RNA in controls and 42.5% (37.8, 46.5) in TP cultures. This corresponds to a reduction of 8.8%. To estimate the fold increase in mRNA that could account for such a change, one needs to know the % of total RNA that is mRNA. Assuming that mRNA is normally 2% of the total, this suggests a 5.5× fold increase in the amount of mRNA or non-ribosomal RNA relative to ribosomal RNA.

To further estimate the change in rRNA, RNA seq analysis of TP and control total RNA samples was undertaken. A custom build of *E. coli* rRNA sequences (Omegabioservices, GA) was used to estimate the fraction of rRNA in samples. The fraction of reads in the control sample that were rRNA was 72% and in TP treated samples it was 68.7%. tRNA was virtually undetectable, or only ~200 out of a total of 7.3× 10⁸reads. This was expected since tRNA is eliminated during isolation, due to its small size. After correcting for an expected control reading of 82% for rRNA, the results suggested a 2.75× fold increase in the amount of mRNA or non-ribosomal RNA in TP treated cells.

The size distribution of the non-ribosomal fraction in both the control and TP RNA samples (FIG. 1) was compared, suggesting an increase in the average mRNA size in TP treated samples. Specifically, the midpoint of the non-ribosomal RNA peak was ~1,700 NT for control samples, and for the TP treated sample it was ~2,000 NT. There are several possible explanations for this observation, but one possibility is an increase in the readthrough of polycistronic operons. Consistent with this idea was the increase in transcripts observed for several anti-terminators in microarray analysis, such as CspA, nusA, Rfah, nusG, and CspE. CspA and nusA were enhanced the most at 3.1 (1.6)× fold, and 2.6 (3)× fold, respectively in RNA microarray analyses (values in parentheses indicate results from RNA seq analysis).

Transcriptional Changes

To get some idea of the impact of RNA stabilization via thiophosphate on specific mRNAs, RNA seq results were analyzed as FPKM (fragments per kilobase pair million) out of all reads including rRNA. This study was designed to give an absolute comparison rather than a relative comparison of transcript levels in total RNA. For control cells a total of 43 million reads of 150 bp in length were analyzed while 73.9 million reads were used in thiophosphate treated samples. The reads were mapped to a reference genome, *E. coli* K-12 substr. MG1655. One of the first things noticed was that many genes were not detected in both treated and control samples. Some of these absences were undoubtedly due to the low coverage resulting from the presence of numerous ribosomal RNA sequences in the preparations. However, even some transcripts readily detected by microarray analysis were not present. Other transcripts were not assessed due to their high copy number and the need for protracted computational time to quantitate. The second thing that was most obvious when comparing the two samples was there were many changes both positive and negative in the levels of transcripts for different genes. The results pointed to significant transcriptional changes induced secondarily via the general stabilization of RNA in vivo with thiophosphate.

For the 4,311 *E. coli* genes examined there was a 1.37× fold increase in the total FPKM counts detected in total RNA from TP treated cells versus controls. The total number of genes with detectable signals was however, only 1,697. Of these, 972 genes showed an increase in FPKM in TP treated cells compared to controls and 725 showed a decrease. The average fold increase was 44× fold (SD 291) with a median of 2.75. There were 10 genes with a fold increase of >900. A total of 66 genes had a fold increase of >100 and 315 had a fold increase of >5. Of those decreased the average fold decrease was 20.4 (SD 93) with a median of 2.4. There were 135 genes decreased more than 10× fold, and 210 more than 5× fold with the maximum decrease observed at 1550×.

Previously it was shown that the use of thiophosphate results in a shift in the distribution of proteins that favors less abundant proteins over more abundant proteins while maintaining soluble cellular protein levels constant (Frayne, 2016, *Mol. & Cell. Biochemistry.* 415, 111-117). The fold changes were suggested to be the result of the preferential accumulation of mRNAs that are less stable over more stable mRNAs. However, in in microarray studies no correlation was observed between mRNA stability and the fold change in relative mRNA abundance between control and thiophosphate treated samples. The average fold change for 10,110 transcripts was −0.1 with a standard deviation of 1.4. Looking at 19 genes with unstable mRNAs (half-lives of less than or equal to 1.4 minutes) revealed an average fold change of 1.0+/−2.8. For a group of 23 mRNAs with half-lives greater than 10 minutes the average fold change was 1.2 with a standard deviation of 2.44.

In *E coli*, 28% of proteins spots detected by 2D gel electrophoresis were significantly changed in previous studies. The present findings, particularly the RNA seq results, supports the idea that transcriptional changes are responsible for most of the changes detected in the levels of cellular proteins. The magnitude of the transcriptional changes observed were well within the range to account for the prior protein results that showed an average ~5× fold change, with 15% increased and 13% decreased. Thus, while all mRNAs are stabilized to some degree via phosphorothioate linkages, transcriptional mechanisms presumably override this impact and result in decreases as well as further increases in the levels of specific mRNAs.

The results raise the possibility that metabolic changes are responsible for the dramatic alteration of the transcriptional profile in thio-phosphate treated cells. The reduction of turnover in RNA could lead to significant savings in energy as RNA turnover itself accounts for 4% of the cells ATP use, RNA polymerization 2.5%, and RNA nucleotide synthesis 10% (Gottschalk 1988, Bacterial Metabolism (2$^{nd}$ Ed). New York: Springer-Verlag). Thus, the use of TP may increase the energy charge of the cell and lead to reprogramming of cells expression profile.

RNA Metabolism

The results indicate there is a significant increase in the amount of non-ribosomal RNA in thio-phosphate treated cells. It is possible, however, that the cell machinery meets this outcome at least in part via an increase RNA synthesis and not just via RNA accumulation alone. Transcripts in relevant pathways were examined, providing support for this idea, by showing an increase in nucleic acid synthetic pathways and a decrease for degradative pathways. For example, in microarray studies, Udp which is used to degrade uridine as a source of energy was significantly reduced 3.2× fold and Upp involved in uracil salvage was increased 2× (FIG. 2). Furthermore, the transcripts for genes involved in UTP and CTP de novo synthesis were also elevated, pyrF 3.7× fold via microarray analysis, as well as pyrH 3.5× fold and pyrG at 2.1× fold via RNA seq analysis (FIG. 2). The expression of other genes in the synthetic pathways for UTP, CTP, and ATP appeared elevated as well, including adk at 3.4× fold via RNA seq analysis and 1.5× fold via microarray analysis. Phosphoribosyl-pyrophosphate synthetase, prsA was also somewhat elevated in both microarray and RNA seq studies (<2×).

RNA modification and processing enzymes were also significantly elevated in TP treated cells (FIG. 2). Several tRNA modification enzymes were elevated at least ~3× fold via microarray analysis (RNA seq results in parentheses) such as dusB (1.18), tadA, and trmA. Several proteins involved in the processing, modification, or binding of rRNA were also significantly elevated at least 3.4× fold, such as rlmH, and yqgf (also elevated 4.64× via RNA seq). In addition, a ribosomal silencing factor, rsfs, was decreased 19× fold via RNA seq analysis. An RNA chaperone antiterminator, cspA was also elevated 3.1× fold via microarray and 1.6× fold via RNA seq. Furthermore, the translation initiation factors, infB and ycih were elevated 3.1× fold and 3.3× fold respectively in microarray studies, as well as via RNA seq analysis at 3× fold and 8× fold, respectively. tRNA synthetases also appeared to be elevated. Microarray analysis showed an average increase of 1.24× fold for 20 genes while RNA seq analysis showed an average increase of 11.7× fold for the 13 tRNA synthetases detected.

The transcripts for the RNA polymerase sigma factor rpoS, were elevated in TP treated samples. Namely, rpoS was elevated 3× fold in microarray studies and 2.3× fold in RNA seq results. This sigma factor is normally increased during late log and is associated with the transition to stationary phase. rpoS is regulated at many levels but even genes involved in its translation were elevated in both microarray and RNA seq analyses, namely, hfq and hn-s. Changes in rpoS could clearly account for some of the transcriptional changes observed. In fact, several genes such as katE, otsA, ybaY, and aidB were elevated ~4-6× fold via RNA seq analysis. Other rpoS regulated genes, however, did not suggest substantial changes.

To try to understand how the phosphorothioate modification of RNA impacts mRNA stability, the fold changes in gene expression for three different groups of mRNAs were examined. The first group consisted of 33 highly unstable mRNAs with half-lives of 3 mins or less, the second group was comprised of 33 mRNAs with average stability (half-lives between 5-7 mins) and the third group of 33 mRNAs with very stable half-lives of 11 mins or more (Selinger et al. 2003, Genome Research 13:216-233). Both the stable mRNA and unstable mRNA classes exhibited the same degree of negative regulation in thiophosphate treated samples versus controls. Namely, 36% of the transcripts for each of these two groups showed negative fold changes. The average stability mRNA class showed a bit less negative regulation, with only 30% demonstrating negative fold changes in thiophosphate versus control samples. The median positive fold changes for the stable and average mRNA classes in thiophosphate treated samples were similar, at 2.7× and 2.6× respectively. In contrast, the unstable class of mRNAs had a median positive fold change of only 1.6×. This result raises the possibility that the phosphorothioate modification may not protect the unstable mRNA class as much from degradation, or that such transcripts are more tightly controlled.

To see if protein abundance correlated with fold changes in mRNA using TP treated cells, transcripts for 18 of the most abundant proteins in *E. coli* were analyzed (Wang et al. 2015, Proteomics 15(18): 3163-8). This group had an average fold change (+ and − summed together) in TP treated cells versus controls of 116× fold with a median of only 1.55× fold. Only 2 out of the 18 genes examined, showed any reduction, and both were still at 80% of normal. While it was harder to detect the transcripts for proteins expressed at low levels via RNA seq analysis, 12 genes expressed at low levels were identified. 58% of these showed negative fold changes in mRNA levels in TP treated bacteria versus controls. 5 of the 18 genes showed fold changes greater than + or −20× fold in TP treated bacteria, and thus exhibited more variability than the other classes of mRNA.

Previous studies using thiophosphate indicated that less abundant proteins may be enhanced at the expense of more abundant proteins (Frayne 2016, Mol Cell Biochemistry 415:111-117). In this regard, transcripts for the several less abundant proteins examined above, exhibited a much higher variability in fold changes with thiophosphate treatment, some showed large increases which may account for the previous findings. In addition, for 18 of the most abundant *E. coli* proteins analyzed, while almost all showed an increase in transcripts with thiophosphate treatment, these increases were much more modest relative to the transcripts for less abundant proteins. It is still possible that increased competition for limiting ribosomes due to increased levels of total mRNA, impacts the translation of more abundant proteins, and/or that other translational mechanisms are at work.

Amino Acid Metabolism

Significant increases in the transcripts for genes in involved in histidine and tryptophan synthesis were detected in thio-phosphate treated cells using RNA seq (FIG. 2). Both histidine and tryptophan need PRPP as a precursor for their synthesis and thus the predicted increase in PRPP likely explains their elevation. The following genes had transcripts elevated in the histidine pathway: hisG (4.6×), hisI (5×), hisA (6.2), hisH (28×), hisB (162×), hisC (117×) and hisD (10.9×). The following genes had transcripts elevated in the tryptophan pathway: tryD (443×), trpE (541×), trpD (443×), trpC (606×), trpA (1049×), and trpB (1955×). In contrast, the pathways for cysteine and leucine biosynthesis appeared to be significantly decreased using RNA seq. Transcripts for Leu A, C, and D were reduced ~500× fold each in thiophosphate treated cells. Furthermore, transcripts for cysM and cysK, were reduced 292× and SOX fold respectively. It is interesting that both cysteine and leucine require acetyl-CoA for their synthesis. It seems possible that the decrease in these two amino acids may be due to the siphoning off of acetyl-CoA for fatty acid synthesis (see below).

Fatty Acid Metabolism

In general, lipid biosynthesis was elevated with an increase in all mRNAs involved in fatty acid synthesis using both microarray and RNA seq analysis (indicated in parentheses). FabB and TesA were elevated the most at 3× (98) and 4× (3.5), respectively. However, all of the following gene transcripts were also elevated: FabA, FabG, FabZ, FabI, FabD (3.1), FabH (10.5), FabF, accD (3.39×), accA (19.8×). FabB is the 3' oxyacyl ACP synthetase, while Tes A catalyzes the last step which cleaves the acyl ACP to generate free fatty acids. The synthesis of malonyl CoA was also elevated with increases in accA 1.3 (19.8×), accD 1.4 (3.4×), and accC 3.2 (6.2×).

The synthesis of phospholipids also appeared to be somewhat elevated with increased amounts of mRNA for cdsA (21×), pssA, plsB, clsA, and pgsA. This may be due to the elevated levels of CTP which stimulates phospholipid synthesis. plsB, pgsA, and pssA were enhanced the most at 1.9× fold.

Isoprenoid Metabolism

In Ecoli the non-melavonate pathway is used for isoprenoid synthesis resulting in the formation of polyisoprenoids. The metabolites isopentenyldiphosphate (IPP) and dimethylallyl diphosphate (DMAPP) are both isomers with IPP being the predominant form. The transcripts for genes involved in the synthesis of IPP and DMAPP were all elevated in TP treated cells (RNA seq fold increases in parentheses): dxs (101), dxr, ispD (2), ispE (1.8), ispF (2.6), ispG, ispH (2.2), and idi (3.57). Dxs and ispD were enhanced the most at 2.5× fold in microarray studies relative to the others at ~1.3× fold. This pathway appeared to feed into the synthesis of undecaprenyl phosphate, a lipid carrier molecule transporting hydrophilic peptidoglycan precursor molecules. The genes involved in the synthesis of undecaprenly phosphate were all elevated in microarray and RNA seq analysis, especially, ispA (154×) and bacA (12×) via RNA seq. This pathway is also used for the synthesis of peptidoglycans and lipopolysaccharides. Several genes involved in peptidoglycan synthesis showed dramatic increases via RNA seq analysis such as murG (199×), murF (250×), murD (144×), murE (152×), ddlB (30×), and murC (26×). Other genes involved in peptidoglycan synthesis were also elevated including ftsI at 1.6× (109), dacA 3.6× fold, idtC 5.2× (3.6) and idtB 2× (164).

Morphological Changes

To see if any morphological changes were occurring the bacteria were examined using bright field microscopy. Both *E. coli* K12 and JM109 strains were examined and both cultures exhibited a distinct filamentous morphology by 12 hrs in thiophosphate media (FIG. 3C). For both bacteria, morphological changes could be detected as early as 2 hrs. where the bacteria appeared as pairs "stuck" together. To test whether this morphology was due to a nutritional deficiency K12 cells were grown in LB broth with 2.7 g of thiophosphate per liter. Filamentous growth was not observed when using LB media with thiophosphate at 12 hrs of growth. However, the bacteria did still exhibit a paired phenotype (FIG. 3B). Note other species such as *Bacillus* do not exhibit this phenotype.

To further explore the basis for the filamentous phenotype K12 bacteria were grown in a semi-synthetic media, where yeast extract is added but otherwise no peptone or exogenous amino acids are added (Frayne, (2016). Mol. & Cell. Biochemistry, 415, 111-117. doi:10.1007/s11010-016-2681-61). In this media, filaments were detected by 8 hrs and by 2 hrs paired bacteria could be seen, as before with minimal media. In the 8 hr sample, however, the view was more mixed compared to that seen with minimal media, as both filamentous bacteria and some shorter and more normal appearing bacteria were observed. When amino acids were added to the semi-synthetic media containing thiophosphate, the bacteria exhibited good growth, but the morphology was mixed with both long filamentous and shorter bacterial cells. The results suggest the filamentous phenotype is more stringent for thiophosphate and the free ortho phosphate in the peptone part of LB alleviates this. The addition of amino acids assisted in recovering the paired phenotype in LB with thio-phosphate.

This filamentous phenotype is likely due to a decrease in the Nlpl protein, as mutations in this gene result in a filamentous phenotype, though at higher temperatures of 42° C. (Ohara, et al., 1999, J. of Bacteriology, 181(14), 4318-4325). The Nlpl protein is deceased 32× fold in thiophosphate treated cells. With thiophosphate this phenotype occurs at ordinary temperatures in minimal medias with the lowest levels of ortho-phosphate.

PRPP Production

*Bacillus megaterium* strain ATCC 15117 (U.S. Pat. No. 3,238,110 & 3,748,232) was used to examine the increased production of AICA using thio-phosphate. Cells were cultured at 26-30° C. for 4 days with 4 g/L of thio-phosphate or normal phosphate (1 g/L). After 24 hrs growth was the same but by day two the thio-phosphate cells grew a bit slower and recovered by the third day to normal or 60% of normal levels. The cells were pelleted, and the supernatant was acidified to pH 2 to help remove unwanted amino acids. The samples were then diluted with one volume of water and bound to activated charcoal with shaking for 2 hrs. (2 grams/20 ml) at room temp. The charcoal was collected on a filter with filtration and washed with 0.01 N HCl. AICA was then eluted with a solution of ethanol/ammonium hydroxide/water at a 1:1:2 ratio using a volume equivalent to the original supernatant. The samples were then separated and analyzed on Whatman chromatography paper using a solvent mixture of 50% butanol, 15% ethanol, and 35% water. The results indicated a ~2× fold increase AICA per volume of cells. TP treated cells exhibited less growth at day 2 with variable recovery by day 4 from 60-100% of controls.

Histidine and tryptophan were added to fermentation reactions to enhance AICA yield by blocking the endogenous synthesis of these amino acids. Using 100 mg of each amino acid per liter resulted in cell lysis of TP cells by day 4. Fermentation reactions were typically initiated with 1.5 ml of overnight growth in nutrient broth which was then diluted into 50 ml of the reaction media. Using twice as many starter cells and only 50 mg each of his and trp resulted in a 5-6× fold cell specific yield of AICA in TP treated cells. Despite the high activity, the growth of these cells was inhibited, almost in parallel with the amount of AICA secreted.

What is claimed is:

1. A method for increasing the levels of PRPP (phosphoribosyl diphosphate) in *E. coli*, by reducing PRPP consumption for RNA synthesis via the inhibition of RNA degradation, comprising:
   a. preparing cell culture media depleted of phosphate
   b. adding thio-phosphate as the sole source of phosphate to the media
   c. culturing cells in the modified media such that most mRNAs and rRNAs are modified with phosphorothioate linkages.

2. The method of claim 1 enhances the flux of PRPP (phosphoribosyl diphosphate) towards the synthesis of histidine, tryptophan, or AICAR (5-aminoimidazole-4-carboxamide ribonucleotide) in cells, including cells with one or more mutations in the tryptophan or histidine biosynthetic pathways.

3. The method of claim 1 wherein the modified media of step c includes 50 mg/L each of histidine and tryptophan.

4. A method to enhance the production of the secreted form of AICAR (5-aminoimidazole-4-carboxamide ribonucleotide), said method comprises bacteria producing AICA (5-aminoimidazole-4-carboxamide ribonucleoside) strains obtained from *Bacillus megaterium, Brevibacterium ammoniagenes, Bacillus subtilis*, or *E. coli* comprising:
  a. preparing cell culture media depleted of phosphate
  b. adding thio-phosphate as the sole source of phosphate to the media
  c. culturing cells in the modified media such that most mRNAs and rRNAs are modified with phosphorothioate linkages.

5. The method of claim 4 wherein the modified media of step c includes 50 mg/L each of histidine and tryptophan.

\* \* \* \* \*